(12) United States Patent
Tehrani

(10) Patent No.: US 8,701,665 B2
(45) Date of Patent: Apr. 22, 2014

(54) AUTOMATIC CONTROL SYSTEM FOR MECHANICAL VENTILATION FOR ACTIVE OR PASSIVE SUBJECTS

(76) Inventor: Fleur T Tehrani, Anaheim, CA (US)

( * ) Notice: Subject to any disclaimer, the term of this patent is extended or adjusted under 35 U.S.C. 154(b) by 1157 days.

(21) Appl. No.: 12/509,457

(22) Filed: Jul. 25, 2009

(65) Prior Publication Data

US 2011/0017214 A1  Jan. 27, 2011

(51) Int. Cl.
*A61M 16/00* (2006.01)
(52) U.S. Cl.
USPC .................................. 128/204.23; 128/204.18
(58) Field of Classification Search
CPC ...................... A61M 16/00; A61M 2016/0069; A61M 2016/0051; A61M 2016/0039; A61M 2016/0021; A61M 126/0066
USPC .............. 128/203.14, 204.18, 204.21–205.23
See application file for complete search history.

(56) References Cited

U.S. PATENT DOCUMENTS

| 4,986,268 A * | 1/1991 | Tehrani | 128/204.22 |
| 5,044,362 A | 9/1991 | Younes | |
| 5,107,830 A * | 4/1992 | Younes | 128/204.18 |
| 5,884,622 A | 3/1999 | Younes | |
| 6,257,234 B1 * | 7/2001 | Sun | 128/204.18 |
| 6,575,163 B1 * | 6/2003 | Berthon-Jones | 128/204.18 |
| 2007/0163590 A1 * | 7/2007 | Bassin | 128/204.23 |
| 2008/0236582 A1 | 10/2008 | Tehrani | |

OTHER PUBLICATIONS

Otis AB, Fenn WO, Rahn H, "Mechanics of breathing in man," Journal of Applied Physiology, vol. 2, pp. 592-607, 1950.
Tehrani, F., Rogers, M, Lo, T., Malinowski, T., Afuwape, S., Lum, M., Grundl, B., and Terry, M., "A dual closed-loop control system for mechanical ventilation," Journal of Clinical Monitoring and Computing, vol. 18, No. 2, pp. 111-129, 2004.

\* cited by examiner

*Primary Examiner* — Melanie Hand
*Assistant Examiner* — Ned T Heffner
(74) *Attorney, Agent, or Firm* — One LLP

(57) ABSTRACT

A method and an apparatus for controlling a ventilator to automatically adjust ventilation assistance to an active or passive subject. The method includes determining volume and flow rate of gas to the patient during inspiration on an ongoing basis, and generating control signals in proportion to the volume and flow rate of gas to the patient wherein proportionality factors, and support levels for the elastic and resistive components of pressure are automatically adjusted by the ventilator. The ongoing pressure applied by the ventilator is a sum of elastic and resistive pressures that are automatically controlled by the system. When the patient breathes spontaneously, the support levels are automatically adjusted based on the patient's requirements. If the patient does not breathe spontaneously, the ventilator provides ventilation at an optimal level and rate. The method may be used in weaning or in a management phase of ventilation.

19 Claims, 3 Drawing Sheets

AUTOMATIC CONTROL SYSTEM FOR MECHANICAL VENTILATION FOR ACTIVE OR PASSIVE SUBJECTS

BACKGROUND OF THE INVENTION

1. Field of the Invention

The present invention relates to mechanical ventilators, and more specifically, to a ventilator control system that automatically adjusts a supply of breathable gas to an active or passive subject to achieve an automatically determined support level.

2. Description of Related Art

Mechanical ventilation is a treatment technique for provision of full or partial respiration assistance to humans or animals with respiratory failure or those who due to surgeries or various other medical conditions cannot breathe on their own. During the course of this life-saving treatment, it is of paramount importance to provide optimal therapy to patients. The amount of ventilation needs to be adjusted in accordance with patient's requirements and the frequency of delivered breaths should be close to the natural respiration rate of the patient. Provision of inappropriate treatment can cause numerous untoward conditions in patients and induce asynchrony between the machine and the patient. Lack of synchrony between the patient and the ventilator can significantly increase work of breathing, necessitate administration of sedatives, prolong the treatment and delay weaning which can all cause complications that may lead to increased mortality and morbidity rates of patients on mechanical ventilation.

There have been many advances in mechanical ventilation in the past several decades. U.S. Pat. No. 4,986,268 (Tehrani) disclosed a novel technique for mechanical ventilation. Using that technique, tidal volume and respiration rate were automatically adjusted by the ventilator based on the bodily requirements of the patient. In that invention, the frequency of delivered breaths was automatically adjusted to minimize the work rate of breathing based on the changing respiratory mechanics of the patient. This was done to provide a breathing pattern that was close to natural for the patient and help synchronize the ventilator with the patient. This system was later adopted in ventilators and has been in use in practice for a number of years.

In order to improve mechanical ventilation during the weaning phase of the treatment, a system for automatic control of weaning was disclosed later in U.S. patent application Ser. No. 11/841,806. In an embodiment of that invention, the ventilator's output is adjusted automatically during weaning based on the strength of the patient's spontaneous breathing.

U.S. Pat. Nos. 5,044,362 and 5,107,830 (Younes) described a novel technique for mechanical ventilation in which the ventilator applied additional airway pressure during the inspiratory phase of ventilation that was proportional to the patient's own developed airway pressure. In this technique, the volume of gas inhaled by the patient and the rate of gas flow to the patient were measured during inspiration and the pressure applied to the patient's airways by the ventilator was proportional to the elastic and resistive pressures developed by the patient's own inspiratory effort. In this technique, the ventilator followed the patient's spontaneous respiratory pattern, and therefore, there was significant synchrony between the machine and the patient. This technique, which has been used in mechanical ventilators in practice in recent years, is particularly suited to the needs of patients with significant spontaneous breathing activity and is most useful in the weaning phase of the treatment. A major drawback of this system, known as proportional assist ventilation, is that it cannot guarantee the delivery of a minimum amount of ventilation to the patient. This may lead to a hazardous situation if the patient's spontaneous breathing activity weakens with time or if the patient develops dyspnea due to fatigue or other causes.

Therefore, it is necessary to provide ventilatory support in concert with the patient's own breathing pattern that can guarantee the delivery of a minimum required ventilation regardless of the status of the patient and the strength of the patient's spontaneous breathing activity.

SUMMARY OF THE INVENTION

The present invention provides a method and apparatus for automatically controlling a ventilator, wherein the volume and flow rate of inspiratory gas to the patient are measured by the system on an ongoing basis (continually during inspiration). The pressure support generated by the system is the sum of elastic and resistive components of pressure, where the elastic component of pressure is proportional to the measured inspiratory gas volume, and the resistive component of pressure is proportional to the measured flow rate of the inspiratory gas. The proportionality factors of the elastic and resistive pressure components in proportion to said volume and flow rate of the inspiratory gas and the elastic and resistive pressure support levels applied by the ventilator are determined and adjusted automatically by the ventilator. The adjustments may be made in view of the measured ventilation and the amount of the patient's required ventilation determined by the ventilator. The system may also adjust the proportionality factors and support levels automatically to prevent fatigue if the work of breathing increases significantly. For passive patients or in case of development of apnea, the ventilator may determine the amount of required ventilation and the rate of respiration to minimize the work rate of breathing. In that case, the ventilator may deliver mandatory breaths based on the calculated required tidal volume at the calculated optimal rate to the patient.

The present invention realizes many advantages over the prior art. While it achieves a desired synchronization between the patient and the ventilator, it guarantees that the patient receives a minimum required ventilation regardless of the strength of the patient's spontaneous breathing effort, both passive and active patients can be treated by the system, and it may be used in the management as well as the weaning phase of ventilatory treatment.

BRIEF DESCRIPTION OF THE DRAWINGS

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims. It is understood that the invention is not limited to the precise arrangements and instrumentalities shown in the drawings which show a presently preferred form of the invention. Component parts shown in the drawings are not necessarily to scale, and may be exaggerated to better illustrate the important features of the invention. In the drawings, like reference numerals designate like parts throughout the different views, wherein:

DETAILED DESCRIPTION OF THE INVENTION

Figure 1:
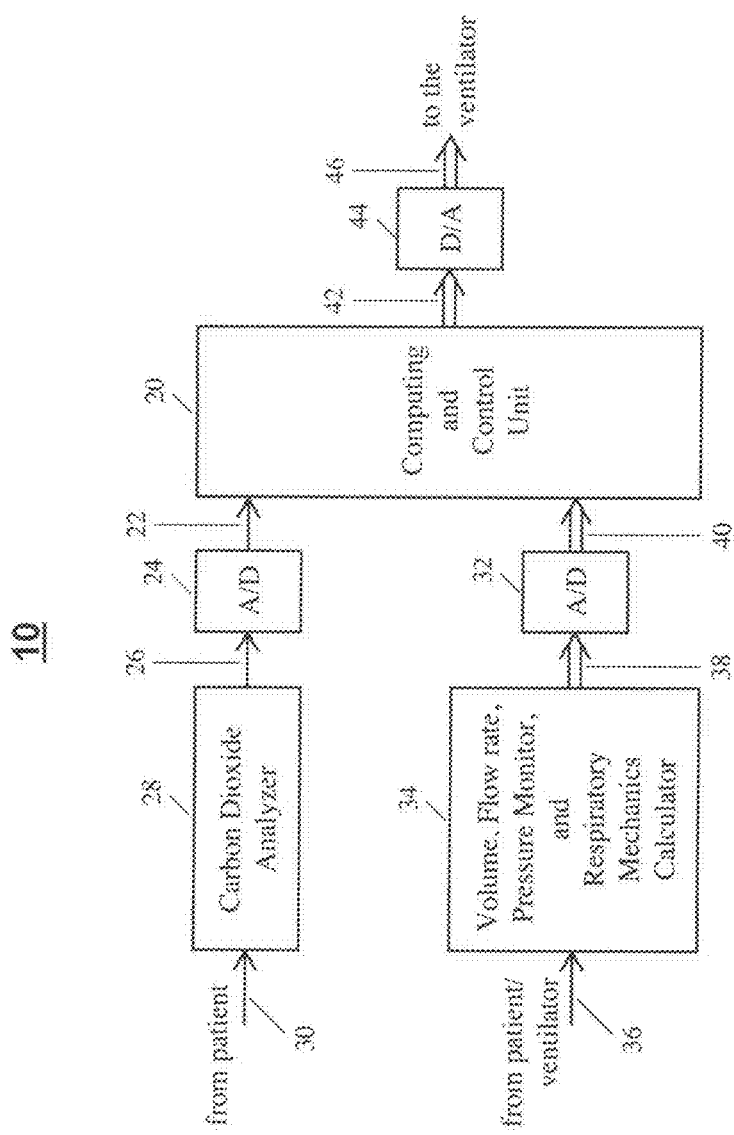
FIG. 1 is a schematic representation of one embodiment of an apparatus for carrying out a method for automatically controlling mechanical ventilation according to the invention.

The following disclosure presents exemplary embodiments of the invention for a ventilator control system. In this system, the volume and flow rate of the inspiratory gas are measured on an ongoing basis (i.e. continually) during inspiration. The pressure support level provided by the ventilator is automatically adjusted based on said measurements in order to adjust a supply of breathable gas to a patient or other user to ensure a minimum required ventilation, and/or to prevent dyspnea and fatigue, while preserving synchrony between the patient and the ventilator. One objective of the invention is to provide appropriate ventilation assistance to a patient regardless of whether the patient is breathing in an active or passive state. Another objective of the invention is to assure that the patient receives a comfortable ventilation assistance treatment in synchrony with the patient's natural breathing regardless of whether the patient is active or passive.

General Description of the Invention

In a ventilatory system known as proportional assist ventilation, for example, as disclosed in U.S. Pat. No. 5,107,830 to Younes, the ventilator provides additional pressure support in proportion to the patient's own inspiratory effort. The pressure applied by the ventilator to the patient's airways in this system is:

$$P_{aw} = K_1 V + K_2 V' \quad (1)$$

Where $P_{aw}$ is the pressure applied by the ventilator, V is the volume of gas inhaled by the patient, V' is the rate of gas flow to the patient, $K_1 V$ is the elastic component of pressure support, $K_2 V'$ is the resistive pressure support provided by the ventilator, and $K_1$ and $K_2$ are proportionality factors for elastic and resistive pressures respectively. The pressure developed by the patient's own effort can be written as:

$$P_{muscle} = KV + K'V' \quad (2)$$

Where $P_{muscle}$ is the pressure developed by the patient, K is the patient's respiratory elastance and K' is the patient's airway resistance. Concentrating on the elastic components of pressure only, KV represents the elastic pressure developed by the patient's muscles and $K_1 V$ is the added response of the ventilator. By using a step-by-step analysis, in the 1$^{st}$ step, the total elastic pressure applied to the patient's airway rises to $V(K+K_1)$. This amount of pressure increases the patient's gas intake to $V(K+K_1)/K$. This volume is then multiplied by $K_1$ to produce the total amount of elastic pressure applied by the ventilator in the next step as:

$$P_{aw} = K_1 \left[ \frac{V(K+K_1)}{K} \right] = K_1 V + K_1^2 \frac{V}{K} \quad (3)$$

Therefore, the total elastic pressure including the elastic pressure generated by the patient's muscle becomes:

$$P_{elastic}(\text{total}) = KV + K_1 V + \frac{K_1^2}{K} V \quad (4)$$

Therefore, the resulting inhaled volume rises to the ratio of this pressure to the patient's respiratory elastance, K. This volume will be:

$$\text{Volume} = V + \frac{K_1}{K} V + \left(\frac{K_1}{K}\right)^2 V \quad (5)$$

Then at the next step, the total amount of elastic pressure applied by the ventilator rises to the product of this volume and the proportionality factor $K_1$, which will be:

$$P_{aw} = K_1 V + \frac{K_1^2}{K} V + \frac{K_1^3}{K^2} V \quad (6)$$

If this iterative analysis is continued, the total elastic pressure applied by the ventilator turns out to be:

$$P_{aw} = K_1 V + \frac{K_1^2 V}{K} + \ldots + \frac{K_1^n V}{K^{n-1}} \quad (7)$$

Which can be rewritten as:

$$P_{aw} = K_1 V \left[ 1 + \frac{K_1}{K} + \ldots + \left(\frac{K_1}{K}\right)^{n-1} \right] \quad (8)$$

If n tends to be large:

$$P_{aw} = K_1 V [1 + \alpha + \alpha^2 + \alpha^3 + \ldots \ldots \alpha^{n-1} \ldots ] \quad (9)$$

where:

$$\alpha = \frac{K_1}{K}$$

The geometric series inside the brackets in equation 9 converges only if $\alpha<1$ (i.e. $K_1<K$). In that case:

$$P_{aw} = \frac{K_1 V}{1-\alpha} \quad (10)$$

Where $P_{aw}$ in equation 10 is the total elastic pressure delivered by the ventilator. As can be seen, if $\alpha \geq 1$, the series inside the brackets in equation 9 will not converge, and as a result, the system will be unstable. A similar analysis on the resistive component of pressure yields that:

$$P_{aw}(\text{resistive}) = \frac{K_2 V'}{1-\alpha'} \quad (11)$$

where:

$$\alpha' = \frac{K_2}{K'}$$

$P_{aw}$(resistive) is the resistive component of pressure delivered by the ventilator in response to patient effort and α' must also be less than 1 for the system to be stable.

Therefore, the total elastic pressure as the sum of the elastic component of the patient muscle pressure, KV, and the elastic component of pressure delivered by the ventilator, $P_{aw}$, from equation 10 becomes:

$$\text{Total elastic pressure} = V\left[K + \frac{K_1}{1-\alpha}\right] \quad (12)$$

where V is the volume of gas inhaled by the patient's own effort.

For this system to be stable, α and α' which are the support levels for elastic and resistive pressures respectively, must be less than 1, and they can be equal. The total volume of gas inhaled during inspiration can be found by dividing the total elastic pressure from equation 12 above by the patient's respiratory elastance, K as:

$$\text{Total volume} = \frac{V\left[K + \frac{K_1}{1-\alpha}\right]}{K} \quad (13)$$

Which yields:

$$\text{Total volume} = V\left[\frac{1}{1-\alpha}\right] \quad (14)$$

The main advantage of the above-described system of ventilation is that the ventilator follows patient's effort and there is significant synchrony between the patient and the machine. However, there is no guarantee in this system that the patient receives adequate ventilation. For example, if the patient's spontaneous effort decreases with time, the machine's support also proportionately decreases which can have serious consequences for the patient. The present invention aims at correcting this deficiency by automatically adjusting the level of support provided by the ventilator. In the system of the present invention, the patient's required ventilation is calculated by the machine and compared with the measured ventilation. The support level is adjusted as follows so that the patient receives adequate ventilation. If required minute ventilation, RMV, is calculated, it can be expressed using equation 14 as follows:

$$RMV = f_{mean} v_{mean} \left[\frac{1}{1-\alpha_1}\right] \quad (15)$$

Where $V_{mean}$ is the average volume inhaled by the patient using the patient's own effort, $f_{mean}$ is the average rate of breathing, and $\alpha_1$ is the elastic pressure support level (which can be equal to the resistive pressure support level) required to provide the patient with his/her required minute ventilation, RMV.

The average measured minute ventilation, AMMV, can be expressed using equation 14 as:

$$AMMV = f_{mean} v_{mean} \left[\frac{1}{1-\alpha}\right] \quad (16)$$

Where α is the set support level. Dividing equation 16 by equation 15 yields:

$$\frac{AMMV}{RMV} = \frac{1-\alpha_1}{1-\alpha} \quad (17)$$

Equation 17 can be rearranged as:

$$\alpha_1 = 1 + \frac{AMMV}{RMV}(\alpha - 1) \quad (18)$$

Therefore, $\alpha_1$, which is the required support level necessary to deliver the required ventilation can be calculated from equation 18 and automatically adjusted. If more push is desired such as in the weaning phase, RMV used in equation 18 may be a fraction of the actual required minute ventilation (e.g., 80% of the actual required value). In that case the required support level may be calculated as:

$$\alpha_1 = 1 + \frac{AMMV}{RMV} \cdot \frac{\alpha - 1}{\beta} \quad (19)$$

where β may be a weaning factor (e.g., 0.8). It should be noted that the required and average ventilation values used in equations 18 and 19 above do not have to be over one minute and can be taken over alternative desired periods of time such as over the interval of several breaths.

This system can also watch for the patient's work of breathing and increase the support level if the work of breathing increases significantly to prevent fatigue and dyspnea. Furthermore, the system of the present invention may provide optimal ventilation at a rate which may be the optimal rate of breathing to minimize the work rate of breathing to passive patients (i.e. patients who do not have spontaneous breathing activity).

Therefore, by using the technique of the present invention, it can be guaranteed that the patient receives a minimum required ventilation regardless of the strength of the patient's spontaneous breathing activity. The ventilator automatically adjusts its support level (α or $\alpha_1$) to provide sufficient ventilation to the patient. The ventilator can also watch the patient's work of breathing and adjust the support level if the work of breathing increases in order to prevent fatigue and dyspnea.

The following example shows how a new support level can be calculated for a spontaneously breathing patient by using a preferred method of this invention.

EXAMPLE

During ventilatory treatment, the average measured minute ventilation, AMMV, is calculated to be 5 lit/min, the required minute ventilation, RMV, is calculated to be 7 lit/min, and the support level, $\alpha$, is 0.5. Using equation 18, the new support level is calculated as:

$$\alpha_1 = 1 + (AMMV/RMV)(\alpha-1) = 1 + (5/7)(0.5-1) = 0.64$$

If more push is required in the weaning phase, and the weaning factor $\beta$ is 0.8, then the new support level is calculated by using equation 19 as:

$$\alpha_1 = 1 + (AMMV/RMV)(\alpha-1)(1/\beta) = 1 + (5/7)(0.5-1)(1/0.8) = 0.55$$

Therefore, the new support level can be adjusted accordingly.

Description of the Preferred Embodiments

Referring now to the drawings, wherein like numerals represent like elements, there is illustrated in FIG. 1 a schematic representation of an apparatus 10 for carrying out a method of the present invention.

A Computing and Control Unit 20 receives input data 22 from an A/D converter 24. The input 26 to the A/D converter 24 may be provided by a $CO_2$ analyzer 28, which measures the $CO_2$ level of a user or patient 30. The $CO_2$ analyzer may be an end-tidal $CO_2$ analyzer that measures the concentration or the partial pressure of $CO_2$ in the exhaled gas of the patient. Alternatively, the $CO_2$ analyzer may be a transcutaneous $CO_2$ analyzer or an arterial analyzer that measure the blood $CO_2$ content of the patient. The $CO_2$ analyzer 28 and the A/D converter 24 are used in some embodiments of the invention and do not need to be used in some other embodiments as will be described later.

A Volume, Flow rate, Pressure Monitor and Respiratory Mechanics Calculator 34 may measure the volume of inhaled and exhaled gases of the patient, the flow rate of gas to and from the patient, and the airway pressure, and may calculate the patient's respiratory elastance (i.e. reciprocal of respiratory compliance) and airway resistance. Such monitors are well known to those skilled in the art such as monitors that have been used for many years in critical care ventilators or the apparatus that has been described in U.S. Pat. No. 5,884,622. An A/D converter unit 32 may receive data indicative of the measured volume, flow rate, pressure, and respiratory mechanics data on 38 from the monitor and calculator unit 34 and may provide the digitized version of that multiple data 40 to the Computing and Control Unit 20 which may comprise a digital processor or a microcomputer. The Computing and Control Unit 20 may process the input data and generate control signals 42 that may be input to a D/A converter unit 44 before being applied to the ventilator.

Figure 2:
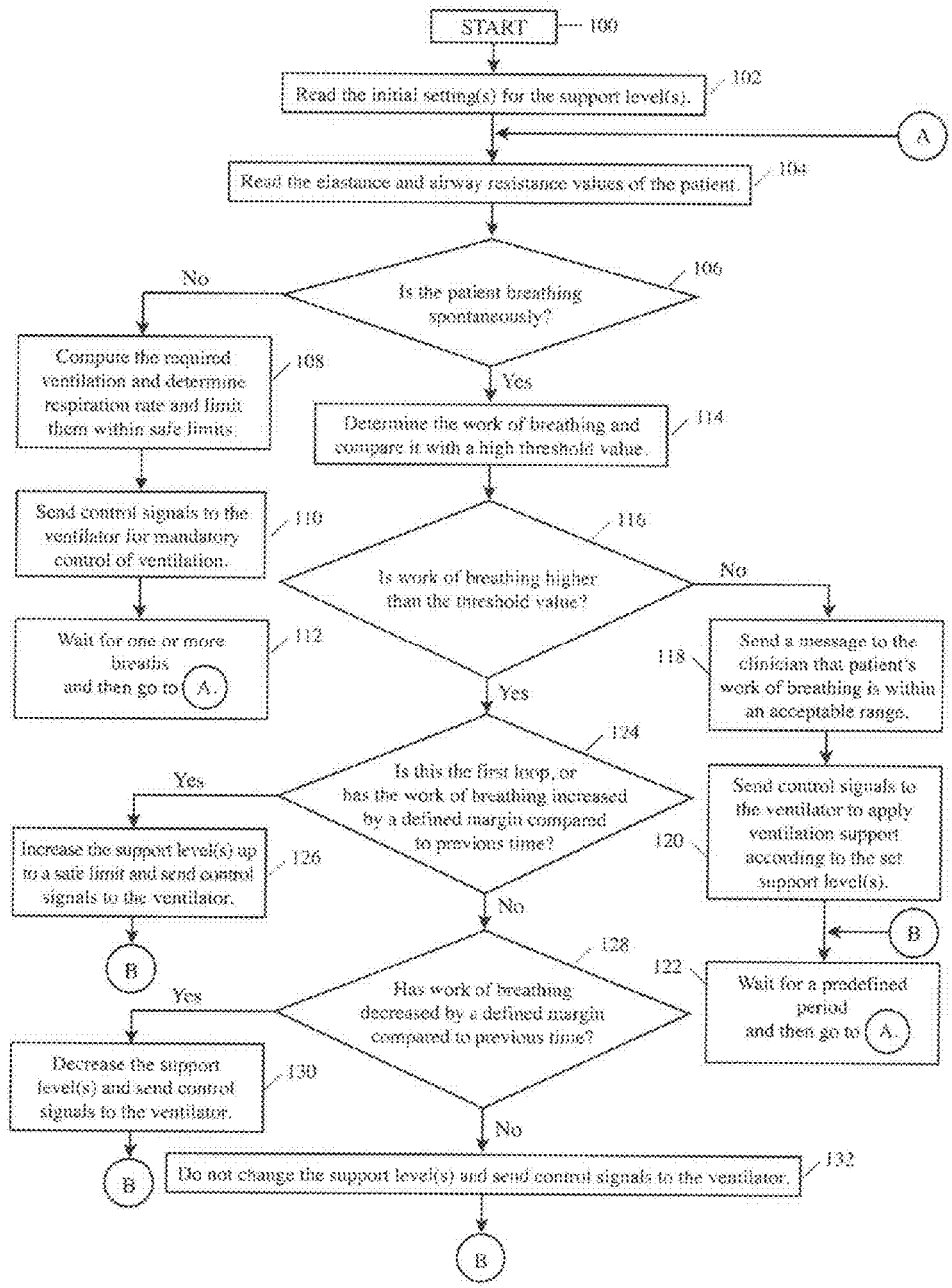
FIG. 2 is a flow chart illustrating a sequence of steps executable by a programmable system in one embodiment of a method for automatically controlling mechanical ventilation according to the invention.

FIG. 2 shows a preferred sequence of steps in one embodiment of the invention that may be executed by a programmable computing system. In this method, the ventilator's support level is automatically controlled to prepare the patient for weaning and prevent fatigue and dyspnea when the patient's work of breathing is significantly higher than normal.

The procedure starts at step 100 and at the next step at 102, the program reads the initial support level(s). A typical initial value may be 0.5. At the next step at A at 104 that follows, the values of patient's respiratory elastance K (which is the reciprocal of respiratory compliance, C), and respiratory airway resistance K' are read. These values may be measured during the breath, for every breath, or intermittently for every several breaths by the monitor and calculator unit 34 in FIG. 1. It may be possible to enter this data and update it over longer periods of time if the patient's respiratory mechanics do not change significantly with time and the support level's maximum value is not close to 1. However, to assure stable operation of the system this data may be provided over short intervals such as during the breath, for every breath, or for every several breaths.

At step 106 that follows, it is checked whether the patient is active, meaning if the patient is breathing spontaneously and triggering the breaths. If the patient is passive (i.e. does not have spontaneous breathing activity), the next step at 108 is performed in which the patient's required ventilation and respiratory rate are determined. The following procedures and equations or their equivalents may be used for these determinations. The required alveolar ventilation may be calculated as:

$$VALV(rest) = 0.061 \times Weight \qquad (20)$$

Where VALV(rest) represents alveolar ventilation in liters per minute at rest and Weight is the ideal body weight of the patient in Kg. The 0.061 factor in this equation may be adjusted based on the patient's basal metabolic rate. Also, VALV(rest) or Weight may be represented in terms of other factors such as patient's height, or basal metabolic rate, or VALV(rest) may be provided by the clinician. In all such or similar cases, the alternative representative factors will be data indicative of Weight and will work the same way.

The $CO_2$ level of the patient may be monitored and used to adjust the level of ventilation. If it is provided, the net effect of $CO_2$ on alveolar ventilation, VAC, may be calculated as:

$$VAC = K_3 [K_5(P_{CO2}-K_4-39.2)+39.2]-K_6 \qquad (21)$$

In equation 21, $P_{CO2}$ is the $CO_2$ level of the patient which may be the end-tidal $CO_2$ pressure measured by a gas analyzer, or the $CO_2$ pressure measured by a transcutaneous or an intra-arterial sensor. $K_5$ is a smoothing factor used to prevent abrupt changes in ventilation and $K_4$ is a factor that can be used to set the desired level of $P_{CO2}$ and may be calculated as:

$$K_4 = P_{CO2}(acceptable)-39.2 \qquad (22)$$

For example, if the acceptable level of $P_{CO2}$ ($P_{CO2}$(acceptable)) is 39.2 mmHg, then $K_4$ from equation 22 will be zero. However, if permissive hypercapnia is used to treat the patient and $P_{CO2}$(acceptable) is for example 48 mmHg, then $K_4$ from equation 22 will be:

$$K_4 = 48-39.2 = 8.8 \text{ mmHg}$$

Typical values of other coefficients used in equation 21 may be $K_3=0.405$, $K_5=0.5/6$, and $K_6=14.88$.

Then alveolar ventilation may be calculated to include the effect of $P_{CO2}$ as:

$$VALV = VALV(rest) \times VAC \qquad (23)$$

It should be noted that if $P_{CO2}$ is very low, VAC from equation 21 can not be negative or zero and should have a minimum acceptable value (e.g., 0.5). Also, if $P_{CO2}$ is not provided, alveolar ventilation, VALV, will be equal to VALV (rest) from equation 20, or it may be provided by the clinician.

After calculation of VALV, the physiological dead space can be estimated by using an empirical equation if it is not provided by measurement. An example empirical equation to calculate the dead space is the following:

$$VD = 0.1698(VALV/60)+0.1587 \qquad (24)$$

Where VD is physiological dead space in liters. Alternatively, VD may be found by using Weight (e.g., VD=0.0026× Weight). Then the total dead space volume may be calculated as:

$$VDt = VD+VDE \qquad (25)$$

Where VDt is total dead space and VDE is the additional dead space due to tubes and connections to the ventilator.

Then the following equation may be used to calculate the optimum frequency of breathing to minimize the respiratory work rate as:

$$f = 60 \times \left[ \frac{-K \times VD + \sqrt{(K \times VD)^2 + 4 \times K \times K' \times \Pi^2 \times \frac{(VALV)}{60} \times VD}}{2 \times K' \times \Pi^2 \times VD} \right] \quad (26)$$

Where K is respiratory elastance in cmH$_2$O/liter, K' is respiratory airway resistance in cmH$_2$O/lit/sec, and f is the optimal breathing rate in breaths/min. Equation 26 may be used to determine the optimal breathing rate of a passive patient. This is done in order to mimic the natural breathing rate of the patient and thereby improve synchrony between the ventilator and the patient and stimulate spontaneous breathing. Equation 26 was used in U.S. Pat. No. 4,986,268 to automatically control the breathing rate of a patient on mechanical ventilation. The unmodified version of this equation was derived in physiology in 1950, in Otis et al., "Mechanics of breathing in Man," Journal of Applied Physiology, vol. 2, pages 592-607, 1950.

The breathing frequency calculated from equation 26 needs to be checked to fall in a safe range. For example, its minimum value can be set at a low frequency such as 6 breaths/min, and its maximum level may be limited to K/5K' to prevent build up of intrinsic positive end-expiratory pressure.

The patient minute ventilation, MV, may then be calculated as:

$$MV = VALV + f \times VDt \quad (27)$$

Then the required tidal volume Vt can be found as:

$$Vt = MV/f \quad (28)$$

Then Vt may be checked to lie within a safe range. For example, the minimum Vt may be defined as (2VD+VDE), and maximum Vt may be the maximum allowed volume set by the clinician. Next, the required peak inspiratory pressure to deliver the calculated Vt may be found as:

$$P_{insp} = K \times Vt + PEEP \quad (29)$$

Where $P_{insp}$ is the required peak inspiratory pressure, and PEEP is the positive end-expiratory pressure. The value of $P_{insp}$ also needs to be checked to fall in a safe range. For example, its minimum level may be set to be 5 cmH$_2$O above PEEP, and its maximum level may be 8-10 cmH$_2$O less than the maximum pressure set on the ventilator or may be directly specified by the clinician.

At the next step 110, the control signals to adjust the pressure support and breathing rate are sent to the ventilator. At the step that follows next at 112, the algorithm will wait for the interval of one or more breaths before it goes back to A.

Back to step 106, if the patient is breathing spontaneously, the program transfers to step 114 at which the delivered work of breathing is determined, which is airway pressure integrated over inspiratory volume. The work of breathing can be found based on the patient's measured values of tidal volume, respiratory elastance, airway resistance, inspiratory flow, and the dimensions of the tubes. This determined work of breathing that may be expressed as the amount of work necessary to deliver one liter of gas to the patient, is compared to a high threshold value set by the clinician (e.g., 1.1 joules/lit). At the next step at 116, if the patient's work of breathing is lower than or equal to the threshold value, step 118 is followed at which a message is generated that patient's work of breathing is acceptable, and at the next step at 120, control signals are sent to the ventilator according to the previous or set support level(s). Then at step 122 at B, the program waits for a predefined period (e.g., 5 minutes) before it goes back to A. It should be noted that if during this period apnea is detected, the program does not wait and automatically transfers to step 108.

Back to step 116, if the patient's work of breathing is higher than the threshold value, the program transfers to step 124. At this point, if this is the $1^{st}$ loop, or if the patient's work of breathing has increased by a defined margin (e.g., at least 10%) compared to the previous time, the support level is increased at step 126. This increase may be defined as proportional to the difference between the high threshold level of work of breathing and the patient's work of breathing in the $1^{st}$ loop, or if not in the $1^{st}$ loop, the increase in the support level may be proportional to the increase in the work of breathing compared to previous time. However, the maximum support level has to be kept less than 1 (e.g., 0.8) for the system to be stable. Afterwards, program transfers to step 122 at B which was described above.

Back to step 124, if it is not the $1^{st}$ loop, and the patient's work of breathing has not increased by a defined margin compared to previous time, then step 128 is performed. At this point, it is checked whether the patient's work of breathing has decreased by a defined margin (e.g., at least 10%) compared to previous time. If it has, then at step 130 that follows, the support level is decreased and this reduction may be proportional to the difference between the patient's work of breathing compared to its previous value. Then control transfers to step 122 at B. Back to step 128, if it is found that patient's work of breathing has not decreased by a defined margin compared to previous time, the next step at 132 is performed in which it is determined that no change in the support level(s) is needed, control signals are sent to the ventilator accordingly and program transfers to B at step 122.

The procedure described in the flow chart of FIG. 2 is performed in one preferred embodiment of the invention in order to adjust the ventilator support level according to the patient's work of breathing. In this procedure, the patient is provided with higher support up to the allowed maximum limit if the patient's work of breathing increases significantly. This is done to prevent the patient from developing fatigue during spontaneous breathing. The system also provides full mandatory control of ventilation providing optimal ventilation at an optimal rate to the patient if the patient is passive or develops apnea as was described above.

Figure 3:
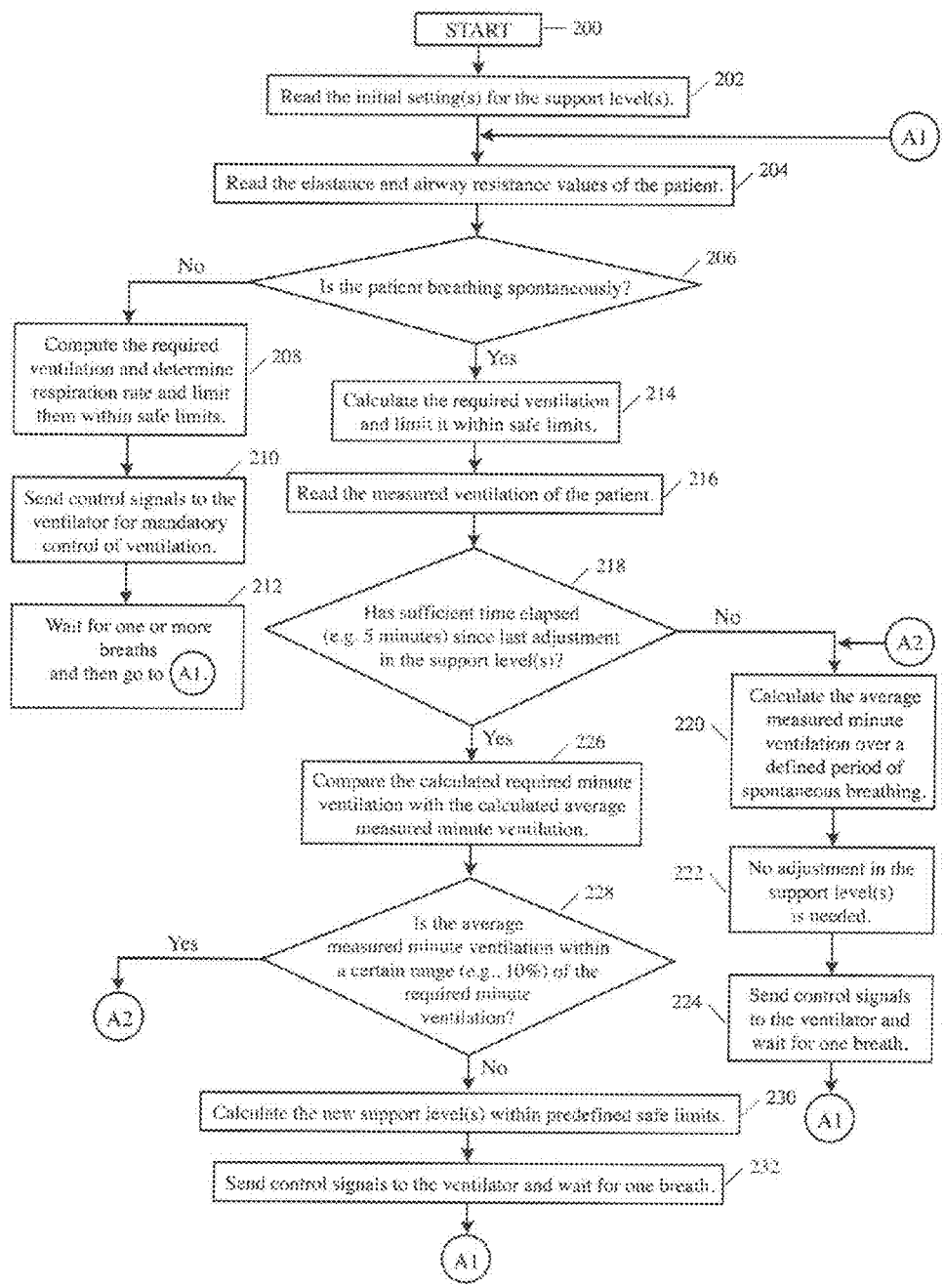
FIG. 3 is a flow chart illustrating another sequence of steps executable by a programmable system in one embodiment of a method for automatically controlling mechanical ventilation according to the invention.

FIG. 3 shows a preferred sequence of steps of the algorithm of a preferred method of the invention. As seen in this Figure, after the start of the program at 200, the program reads the initial setting of the support level(s) at step 202. a typical initial setting may be 0.5. At the next step at A1 which is at step 204, the patient's respiratory elastance and airway resistance values are read. The provision of these values can be done in the same ways that were described in step 104 in FIG. 2 before.

In the next step at 206, it is checked whether the patient is breathing spontaneously. If the patient is not breathing spontaneously, the algorithm transfers to steps 208, 210, and 212 in sequence in which the same procedures and calculations are performed that were carried out in steps 108, 110, and 112 of FIG. 2 respectively, the patient's level and rate of ventilation are computed and controlled by the ventilator as was described before, and then the program returns to A1 at step 204. However, if at step 206 it is found that the patient is breathing spontaneously, at the next step that in this case is step 214, the required minute ventilation, RMV (which is the same as MV), is calculated by using equations 20, 21, 22, 23, 24, 25, and 27 as these equations were described above. For these calculations, f in equation 27, is the measured patient's breathing rate. Also, equations 21, 22, and 23 are only used if patient's $P_{CO2}$ is measured and provided to the system. Otherwise, equations 21, 22, and 23 are not used and VALV will be the same as VALV(rest) from equation 20, or it may be provided by the clinician. It should be noted that the equations used in these steps can be replaced by their equivalents in which case the function of the procedure will not be different from the function described here and therefore, will be the same invention.

After the calculations of step 214, the measured ventilation of the patient is read at step 216. Then at step 218 that follows next, it is checked whether sufficient time has elapsed (e.g., 5 minutes) since the last adjustment in the support level(s). If sufficient time has not passed, then at the next step 220 at A2, the program continues by calculating the average measured minute ventilation (AMMV) value. This calculation is done over a short defined period (e.g., 3 minutes), and if the patient is partly breathing spontaneously, the average value (AMMV) may be calculated over the last period of spontaneous breathing (e.g., over a certain number of consecutive spontaneous breaths). Then at the next step at 222 it is determined that no adjustment in the support level(s) is needed, and at step 224, control signals are sent to the ventilator and the algorithm transfers to A1 at the end of the breath.

Back to step 218, if sufficient time has elapsed since the last adjustment in the support level, program transfers to step 226 in which the required minute ventilation of the patient (RMV which is the same as MV) calculated at step 214 is compared to the average measured minute ventilation, AMMV. At the next step at 228, if AMMV is within a defined range (e.g., 10%) of RMV calculated at step 214, then program transfers to A2 which was described above.

However, if at step 228, AMMV is not within the defined range of RMV, then in the next step 230 that follows, new support level(s) is computed by using equation 18, or if additional push for weaning is required, by using equation 19 that were described earlier. Afterwards, control signals are sent to the ventilator at step 232, and the algorithm transfers to A1 at the end of the breath.

The flow chart shown in FIG. 3 illustrates a preferred procedure carried out in an embodiment of the invention to automatically adjust the ventilator's support level. By using this system it is guaranteed that a minimum ventilation is provided to the patient regardless of the strength of the patient's spontaneous breathing activity. Whenever adjusted, the support level is compared to a defined safe range and limited if necessary to remain within that range in the system of the invention.

Exemplary embodiments of the invention have been disclosed in an illustrative style. The present invention may be embodied in other specific forms without departing from the scope and attributes of the invention as will be understood to those well versed in the art. Accordingly, what is intended to be circumscribed within the scope of the patent warranted hereon are all such embodiments that reasonably fall within the scope of the advancement to the art hereby contributed, and that scope shall not be restricted, except in light of the appended claims and their equivalents.

What is claimed is:

1. A method for automatically controlling a ventilator, comprising:
    (a) determining ongoing volume and flow rate of gas to a patient during inspiration;
    (b) providing respiratory elastance, K, and airway resistance, K', of the patient;
    (c) generating control signals controlling pressure applied by the ventilator as a sum of elastic and resistive components of pressure, the elastic component of pressure having a proportionality factor, $K_1$, proportional to the determined volume of the inspiratory gas, and the resistive component of pressure having a proportionality factor, $K_2$, proportional to the determined flow rate of the inspiratory gas; and
    (d) automatically adjusting the elastic and resistive components of pressure support by automatically finding and adjusting an elastic component of pressure support level, $\alpha=K_1/K$, and a resistive component of pressure support level, $\alpha'=K_2/K'$, and the proportionality factors $K_1$ and $K_2$, based on a comparison between a required ventilation for the patient and an average measured ventilation for the patient.

2. The method of claim 1 further comprising determining the required ventilation for the patient based on data indicative of an ideal body weight of the patient.

3. The method of claim 1 further comprising determining the required ventilation for the patient based on a measured carbon dioxide level of the patient.

4. The method of claim 3 wherein the required ventilation for the patient is determined according to the following equations:

$$VAC=K_3[K_5(P_{CO2}-K_4-P1)+P1]-K_6,$$

$$VALV=VALV(\text{rest})\times VAC,$$

$$VDt=VD+VDE, \text{ and}$$

$$MV=VALV+f\times VDt$$

where VAC is a factor representing a net effect of the patient's $CO_2$ level on alveolar ventilation, and VAC cannot be negative, zero, or less than a predefined value, $K_5$ is a smoothing constant parameter less than or equal to 1, $P_{CO2}$ is the measured carbon dioxide level of the patient, P1 is a normal level of $P_{CO2}$, $K_4$ is a difference between an acceptable level of $P_{CO2}$ for the patient and P1, and $K_4$ is chosen to set a desired level of patient's $P_{CO2}$, $K_3$ and $K_6$ are constants, VALV(rest) is patient's alveolar ventilation at rest in liters per minute proportional to patient's ideal body weight, VALV is patient's required alveolar ventilation in liters per minute, VD is patient's physiological dead space determined as $VD=C_1\times VALV+C_2$ where $C_1$ and $C_2$ are constants, VDE is a dead space due to tubes and connections to the ventilator, VDt is total dead space volume, f is a patient's rate of spontaneous breathing measured by the ventilator per minute, and MV is the patient's required ventilation in liters per minute.

5. The method of claim 1 wherein updated support levels and proportionality factors are determined according to:

$$\alpha_1 = 1 + \frac{AMMV}{RMV}(\alpha - 1)$$

where AMMV is the patient's average measured ventilation per minute, RMV is the patient's required ventilation per minute, α is a prior support level, and $α_1$ is an updated support level equal to updated $K_1/K$, which is also equal to updated $K_2/K'$.

6. The method of claim 1 wherein updated support levels and proportionality factors are determined according to:

$$\alpha_1 = 1 + \frac{AMMV}{RMV} \cdot \frac{\alpha - 1}{\beta}$$

where AMMV is the patient's average measured ventilation per minute, RMV is the patient's required ventilation per minute, β is a factor that is positive and less than 1, α is a prior support level, and $α_1$ is an updated support level equal to updated $K_1/K$, which is also equal to updated $K_2/K'$.

7. The method of claim 1 further comprising determining whether the patient is breathing spontaneously, and if the patient is not breathing spontaneously, then skipping steps (c) and (d), determining a required ventilation for the patient, and based on the patient's required ventilation and the patient's respiratory elastance and airway resistance values, determining an optimal breathing rate for the patient, and providing mandatory ventilation to the patient according to the determined required ventilation and optimal breathing rate.

8. The method of claim 7 wherein the patient's required ventilation is determined based on data indicative of an ideal body weight of the patient.

9. The method of claim 7 wherein the patient's required ventilation is determined based on a measured carbon dioxide level of the patient.

10. The method of claim 7 wherein the patient's optimal breathing rate is determined to minimize respiratory work rate.

11. The method of claim 10 wherein the following equation is used to calculate the optimal breathing rate:

$$f = 60 \times \left[ \frac{-K \times VD + \sqrt{(K \times VD)^2 + 4 \times K \times K' \times \Pi^2 \times \frac{(VALV)}{60} \times VD}}{2 \times K' \times \Pi^2 \times VD} \right]$$

where VALV is a required alveolar ventilation for the patient per minute, VD is respiratory dead space found as $VD = C_1 \times VALV + C_2$, where $C_1$ and $C_2$ are constant parameters, and f is the optimal rate of breathing per minute.

12. An apparatus for automatically controlling a ventilator, comprising:
a computing system;
digital readable memory coupled to the computing system;
one or more transducers providing data to the computing system representing ongoing volume and flow rate of a gas to a patient during inspiration; and
a program stored in the memory, the program when executed by the computing system determining an elastic component of pressure support level, $α = K_1/K$, a resistive component of pressure support level, $α' = K_2/K'$, where $K_1$ and $K_2$ represent proportionality factors for elastic and resistive components of pressure supplied by the ventilator respectively and K and K' represent respiratory elastance and airway resistance of the patient respectively, and also determining a level of ongoing pressure support to the patient as a sum of the elastic and resistive pressures, wherein the elastic and resistive pressure support levels are determined based on a comparison between a required ventilation for the patient and an average measured ventilation for the patient performed by the program, and the ongoing pressure support to the patient is determined based on the elastic and resistive pressure support levels and the data provided by the transducers, and the computing system generating control signals to the ventilator to achieve the determined elastic and resistive pressure support levels and the level of ongoing pressure support.

13. The apparatus of claim 12 wherein the transducers further include one or more monitors for measuring respiratory elastance and airway resistance of the patient.

14. The apparatus of claim 13 wherein the required ventilation for the patient is determined by the program stored in the memory based on data indicative of an ideal body weight for the patient.

15. The apparatus of claim 13 wherein the required ventilation for the patient is determined based on a measured level of carbon dioxide of the patient provided to the computing system by a carbon dioxide analyzer.

16. The apparatus of claim 15 wherein the carbon dioxide analyzer is selected from the group comprising an end-tidal gas analyzer, an arterial gas analyzer, and a transcutaneous $CO_2$ analyzer.

17. The apparatus of claim 13 wherein if the patient does not breathe spontaneously, the program stored in the memory does not determine the support levels and instead determines a required ventilation for the patient and an optimal respiration rate for the patient wherein the patient's optimal respiration rate is determined according to the following equation:

$$f = 60 \times \left[ \frac{-K \times VD + \sqrt{(K \times VD)^2 + 4 \times K \times K' \times \Pi^2 \times \frac{(VALV)}{60} \times VD}}{2 \times K' \times \Pi^2 \times VD} \right]$$

where K is respiratory elastance, K' is airway resistance, VALV is a required alveolar ventilation for the patient per minute input to the program or found from a data indicative of an ideal body weight for the patient, VD is respiratory dead space found as $VD = C_1 \times VALV + C_2$, where $C_1$ and $C_2$ are constant parameters, f is the optimal rate of breathing per minute, and the computing system generates output data indicative of the required ventilation and the optimal respiration rate.

18. The apparatus of claim 13 further comprising one or more A/D converters connected between the transducers and the computing system for converting analog signals from the transducers into digital form.

19. The apparatus of claim 12 further comprising one or more D/A converters for converting digital signals from the computing system to analog signals and supplying the analog signals to the ventilator as the control signals.

* * * * *